(12) United States Patent
Lin

(10) Patent No.: US 11,690,523 B2
(45) Date of Patent: *Jul. 4, 2023

(54) CAROTID ARTERY BLOOD PRESSURE DETECTING DEVICE

(71) Applicants: Shiming Lin, Taipei (TW); BIV MEDICAL, LTD., Caotun Township, Nantou County (TW)

(72) Inventor: Shiming Lin, Taipei (TW)

(73) Assignees: Shiming Lin, Taipei (TW); BIV MEDICAL, LTD., Caotun Township, Nantou County (TW)

(*) Notice: Subject to any disclaimer, the term of this patent is extended or adjusted under 35 U.S.C. 154(b) by 709 days.

This patent is subject to a terminal disclaimer.

(21) Appl. No.: 16/630,663

(22) PCT Filed: Jul. 10, 2018

(86) PCT No.: PCT/CN2018/095173
§ 371 (c)(1),
(2) Date: Jan. 13, 2020

(87) PCT Pub. No.: WO2019/011241
PCT Pub. Date: Jan. 17, 2019

(65) Prior Publication Data
US 2021/0022625 A1    Jan. 28, 2021

Related U.S. Application Data

(60) Provisional application No. 62/604,656, filed on Jul. 17, 2017, provisional application No. 62/604,596, filed on Jul. 13, 2017.

(51) Int. Cl.
*A61B 5/00* (2006.01)
*A61B 5/0245* (2006.01)
(Continued)

(52) U.S. Cl.
CPC ........... *A61B 5/0245* (2013.01); *A61B 5/002* (2013.01); *A61B 5/0004* (2013.01);
(Continued)

(58) Field of Classification Search
None
See application file for complete search history.

(56) References Cited

U.S. PATENT DOCUMENTS

2010/0286607 A1* 11/2010 Saltzstein ............ A61B 5/6848
604/93.01
2016/0166211 A1   6/2016 Brown et al.
2018/0020931 A1*  1/2018 Shusterman .......... A61B 8/04
600/483

FOREIGN PATENT DOCUMENTS

CN  101991436 A  3/2011
CN  102652679 A  9/2012
(Continued)

*Primary Examiner* — Shahdeep Mohammed
(74) *Attorney, Agent, or Firm* — Muncy, Geissler, Olds & Lowe, P.C.

(57) ABSTRACT

The present invention provides a carotid blood pressure detection device, comprising: a first sensing unit, a second sensing unit, and a controller connected or coupled to the first sensing unit and the second sensing unit. The first sensing unit is disposed on a subject's neck and adjacent to a first position of the subject's carotid arteries. The second sensing unit is disposed on the subject's neck and adjacent to a second position of the subject's carotid arteries. The controller derives a mean arterial pressure of a section of the subject's carotid arteries that lies between the first position and the second position of the subject's carotid arteries from pulse wave data measured and obtained by the first sensing unit and pulse wave data measured and obtained by the second sensing unit.

9 Claims, 11 Drawing Sheets

(51) Int. Cl.
 *A61B 5/021* (2006.01)
 *A61B 5/024* (2006.01)
 *A61B 8/04* (2006.01)
 *A61B 7/04* (2006.01)
 *A61B 5/0507* (2021.01)
 *A61B 5/02* (2006.01)

(52) U.S. Cl.
 CPC ...... *A61B 5/02007* (2013.01); *A61B 5/02108* (2013.01); *A61B 5/02125* (2013.01); *A61B 5/02438* (2013.01); *A61B 5/0507* (2013.01); *A61B 5/684* (2013.01); *A61B 5/6823* (2013.01); *A61B 5/6824* (2013.01); *A61B 5/6833* (2013.01); *A61B 5/7275* (2013.01); *A61B 7/04* (2013.01); *A61B 8/04* (2013.01); *A61B 5/02416* (2013.01); *A61B 2562/0247* (2013.01)

(56) References Cited

FOREIGN PATENT DOCUMENTS

| | | | |
|---|---|---|---|
| CN | 104224142 A | | 12/2014 |
| CN | 104414626 A | * | 3/2015 |
| CN | 105708431 A | | 6/2016 |
| CN | 105852832 | * | 8/2016 |
| CN | 105852832 A | | 8/2016 |
| CN | 106725403 A | | 5/2017 |
| WO | WO-2015/004754 A1 | | 1/2015 |
| WO | WO-2016/130083 A1 | | 8/2016 |

* cited by examiner

CAROTID ARTERY BLOOD PRESSURE DETECTING DEVICE

BACKGROUND OF THE INVENTION

1. Technical Field

The present invention relates to a blood pressure detection device, and particularly to a carotid blood pressure detection device for detecting carotid blood pressure.

2. Description of Related Art

The carotid arteries are the main source arteries that supply blood to the brain but are also the predilection sites for atherosclerosis. Carotid arteriosclerosis may lead to brain ischemia or even a severe stroke and is therefore an important risk factor of cerebrovascular disease. Moreover, the presence and degree of carotid arteriosclerosis may reflect to a certain extent the presence and degree of arteriosclerosis of the other major arteries. The carotid arteries are shallow, easy to detect, and hence a clinical window through which to discover arteriosclerosis.

A stroke is a cerebrovascular disease that stems from insufficient blood supply to the brain and that causes damage to the central nervous system, occurring typically in those who are 60 to 70 years old. Apart from such risk factors as hypertension, diabetes, hyperlipidemia, smoking, and family history, atherosclerosis is the most common cause of ischemic strokes. Literature has shown that carotid stenosis-related occlusion accounts for about 20% of the cases of atherosclerosis, hypertension-related lacunar infarct about 20%, occlusion attributable to atrial fibrillation-related arrhythmia 25%, and occlusion of unknown causes 30%. Besides, it has been frequently reported that there is a strong statistical correlation between stenosis of the left or right carotid arteries and a subsequent ischemic stroke that affects the same side of the brain. One study shows that patients with more than 80% stenosis of the carotids are nearly 60 times as likely (92.3% vs 1.5%) to suffer ischemic strokes and other complications at a later time as those with less than 80% stenosis. The same study also found that carotid stenosis and its symptoms aggravate over time. It can be known from the above that the detection and quantitative assessment of carotid stenosis are of paramount clinical importance to the prevention of strokes, and that accordingly the development of a fast-screening method or technique for assessing carotid stenosis is a key issue in stroke prevention.

As stated above, patients with high-percentage carotid stenosis are far more likely to have ischemic strokes and other complications than those with low-percentage carotid stenosis. In addition, carotid stenosis affects cerebral blood volume (CBV), which in turn is closely related to dementia. To prevent strokes and dementia, therefore, clinical detection of carotid stenosis is critical. Methods conventionally used to diagnose carotid stenosis and determine the CBV include, among others, digital subtraction angiography (DSA), magnetic resonance angiography (MRA), and Doppler ultrasound scanning of the carotid arteries. The aforesaid methods, however, are often time-consuming, have their respective limitations, and are consequently unsuitable for fast screening. It is crucial to develop a fast-screening method or technique for carotid stenosis in order to prevent strokes and dementia.

Carotid Doppler ultrasound has many restrictions in terms of engineering and clinical application. For example, due to the cranium, only a limited portion of the carotid arteries (i.e., the portion in the neck) is detectable by Doppler ultrasonography. While the detection area can be increased by using Doppler ultrasound that can penetrate the cranium, the improvement is nominal. As to carotid angiography, a study comparing angiographic results against biopsy sections obtained by carotid endarterectomy shows that carotid angiography has a false negative rate as high as 40%. MRA uses the vector properties of blood flow velocity in an applied magnetic field to determine the condition of the blood vessel under observation, but the anatomical structure of the blood vessel cannot be observed as precisely as with the conventional angiography now that the resulting MRA image is sensitive to blood flow velocity.

BRIEF SUMMARY OF THE INVENTION

Patients with high-percentage carotid stenosis are far more susceptible to ischemic strokes and other complications than those with low-percentage carotid stenosis. Furthermore, carotid stenosis affects the CBV, which is closely related to dementia. To prevent strokes and dementia, therefore, clinical detection of carotid stenosis is critical. Methods conventionally used to diagnose carotid stenosis and determine the CBV include DSA, MRA, Doppler ultrasound scanning, etc. of the carotid arteries, but the foregoing clinical methods for assessing carotid stenosis have their respective limitations and are time-consuming. Taking Doppler ultrasound—the simplest of them all—for example, it takes at least 20 minutes to complete one examination. Angiographic methods such as DSA and MRA take even longer time and entail risks associated with their invasive procedures and the use of contrast agents, which may cause allergic reactions. Computed tomography angiography (CTA), which has become more and more common in recent years, involves risks related to radiation as well as contrast agents. It is therefore imperative to provide those who already had a stroke, who are exposed to the risk factors of strokes, or who have shown the early sign of a stroke (e.g., have had a transient ischemic attack) with a screening method and examination instrument that can rapidly assess the blood flow in, and the level of stenosis of, the carotid arteries.

The objective of the present invention is to provide an innovative technique for detecting carotid blood pressure by using a sensor to measure and screen carotid stenosis and make it a medical detection device suitable for elderly users.

In order to achieve the above objective, the present invention provides a carotid blood pressure detection device, comprising: a first sensing unit is configured to be disposed on a subject's neck and adjacent to a first position of the subject's carotid arteries; a second sensing unit is configured to be disposed on the subject's neck and adjacent to a second position of the subject's carotid arteries; and a controller connected or coupled to the first sensing unit and the second sensing unit, wherein the controller derives a mean arterial pressure of a section of the subject's carotid arteries that lies between the first position and the second position of the subject's carotid arteries from pulse wave data measured and obtained by the first sensing unit and pulse wave data measured and obtained by the second sensing unit; wherein the first sensing unit is a Doppler radar, a pressure sensor, an acoustic wave sensor, an ultrasound sensor, or a photoplethysmographic sensor, the second sensing unit is a Doppler radar, a pressure sensor, an acoustic wave sensor, an ultrasound sensor, or a photoplethysmographic sensor; wherein the mean arterial pressure is obtained through one of the following equation:

$$MAP = a\left(\frac{l_p}{t_{pa}} \times c\right) + b,$$

or $$MAP = A\left(\frac{l_p}{t_{pa}} \times C\right)^2 + B;$$

wherein MAP is the mean arterial pressure; lp is a length of a path between the first position and the second position; tpa is times it takes for a pulse to reach the second position from the first position; and a, b, and c and A, B, and C are correction parameters.

Furthermore, the carotid blood pressure detection device further includes an adhesive patch, and the adhesive patch is provided with the first sensing unit and the second sensing unit.

Furthermore, the adhesive patch is provided with a thyroid cartilage locating hole or a thyroid cartilage locating mark, and the first sensing unit and the second sensing unit are provided on one side of the thyroid cartilage locating hole or the thyroid cartilage locating mark and are properly spaced apart.

Furthermore, the positions at which the first sensing unit and the second sensing unit are respectively provided on the adhesive patch are determined as follows: a starting point position is defined as a position 2.7 cm to 3.3 cm to the left or right of the thyroid cartilage locating hole or the thyroid cartilage locating mark, and a specific direction is defined as the direction that forms an included angle of 135 degrees with the line connecting the starting point position and the thyroid cartilage locating hole or the thyroid cartilage locating mark, wherein the included angle is measured upward from the line connecting the starting point position and the thyroid cartilage locating hole or the thyroid cartilage locating mark; wherein, the first sensing unit is provided at a position that is 0 cm to 4 cm away from the starting point position in the aforesaid direction, and the second sensing unit is provided at a position that is 0 cm to 4 cm away from the starting point position in the same direction and that does not coincide with the first sensing unit.

Furthermore, the carotid blood pressure detection device further includes a communication module connected to the controller.

Furthermore, the communication module performs wireless transmission-based communication, and the applicable wireless transmission methods include Bluetooth, wireless local area network (WLAN), radio frequency identification (RFID), near-field communication (NFC), and Zigbee.

Furthermore, the controller is connected or coupled to a mobile device or a wearable device via the communication module to access the data of the controller through the mobile device or the wearable device.

Furthermore, the first sensing unit is a Doppler radar, a pressure sensor, an acoustic wave sensor, an ultrasound sensor, or a photoplethysmographic sensor.

Furthermore, the second sensing unit is a Doppler radar, a pressure sensor, an acoustic wave sensor, an ultrasound sensor, or a photoplethysmographic sensor.

Furthermore, the first sensing unit and the second sensing unit are spaced apart by a distance ranging from 1 cm to 4 cm.

Furthermore, the positions at which the first sensing unit and the second sensing unit are respectively provided on are determined as follows: a starting point position is defined as a position 2.7 cm to 3.3 cm leftward of a center point defined as peak of the thyroid cartilage of a subject's neck that lies right below the middle point of the subject's lips, and a specific direction is defined as the direction that forms an included angle of 135 degrees with the line connecting the starting point position and the thyroid cartilage locating hole or the thyroid cartilage locating mark, wherein the included angle is measured upward from the line connecting the starting point position and the center point; wherein, the first sensing unit is provided at a position that is 0 cm to 4 cm away from the starting point position in the aforesaid direction, and the second sensing unit is provided at a position that is 0 cm to 4 cm away from the starting point position in the same direction and that does not coincide with the first sensing unit.

In the global medical device market, there has been a considerable demand for carotid stenosis assessment methods that can be easily applied to those who have had a stroke or who are highly prone to cardiovascular disease, and many advanced countries in the world have placed great emphasis on the research and development of carotid stenosis detection methods and instruments. The present invention makes effective use of sensors to detect the pressure of the carotid arteries so that a senior patient can be rapidly screened for carotid stenosis. The invention can be used in a fast-screening test because it effectively reduces the examination time required by such conventional methods as DSA, MRA, and Doppler ultrasound scanning.

DETAILED DESCRIPTION OF THE INVENTION

The details and technical solution of the present invention are hereunder described with reference to accompanying drawings. For illustrative sake, the accompanying drawings are not drawn to scale. The accompanying drawings and the scale thereof are not restrictive of the present invention.

The use of "comprise" means not excluding the presence or addition of one or more other components, steps, operations, or elements to the described components, steps, operations, or elements, respectively. Similarly, "comprise," "comprises," "comprising," "include," "includes," and "including" are interchangeable and not intended to be limiting. As used herein and in the appended claims, the singular forms "a," "an," and "the" include plural referents unless the context dictates otherwise. The terms "a", "an," "the," "one or more," and "at least one," for example, can be used interchangeably herein.

Figure 1:
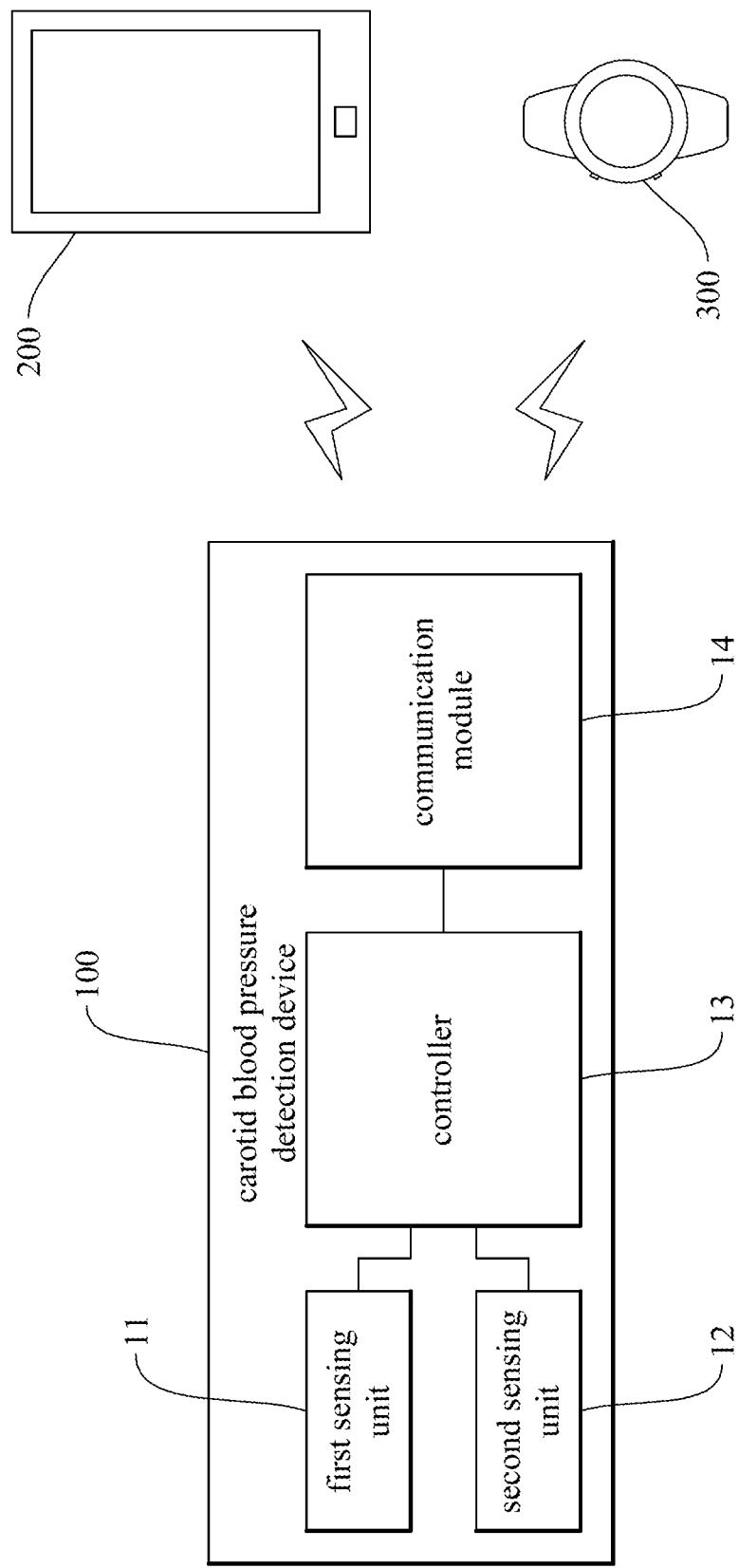
FIG. 1 is a first block diagram of a carotid blood pressure detection device according to the present invention.

Please refer to FIG. 1 for the block diagram of a carotid blood pressure detection device according to the present invention.

The present invention provides a carotid blood pressure detection device 100 as shown in FIG. 1. The carotid blood pressure detection device 100 is configured for use with a mobile device 200 or a wearable device 300, in order for the mobile device 200 or the wearable device 300 to access and process the data measured and obtained by the carotid blood pressure detection device 100.

The carotid blood pressure detection device 100 includes a first sensing unit 11, a second sensing unit 12, a controller 13 connected to the first sensing unit 11 and the second sensing unit 12, and a communication module 14.

In one preferred embodiment, the first sensing unit 11 and the second sensing unit 12 may be, but are not limited to, Doppler radars, pressure sensors, acoustic wave sensors, ultrasound sensors, photoplethysmographic sensors, or the like; the present invention has no limitation in this regard.

Figure 2:
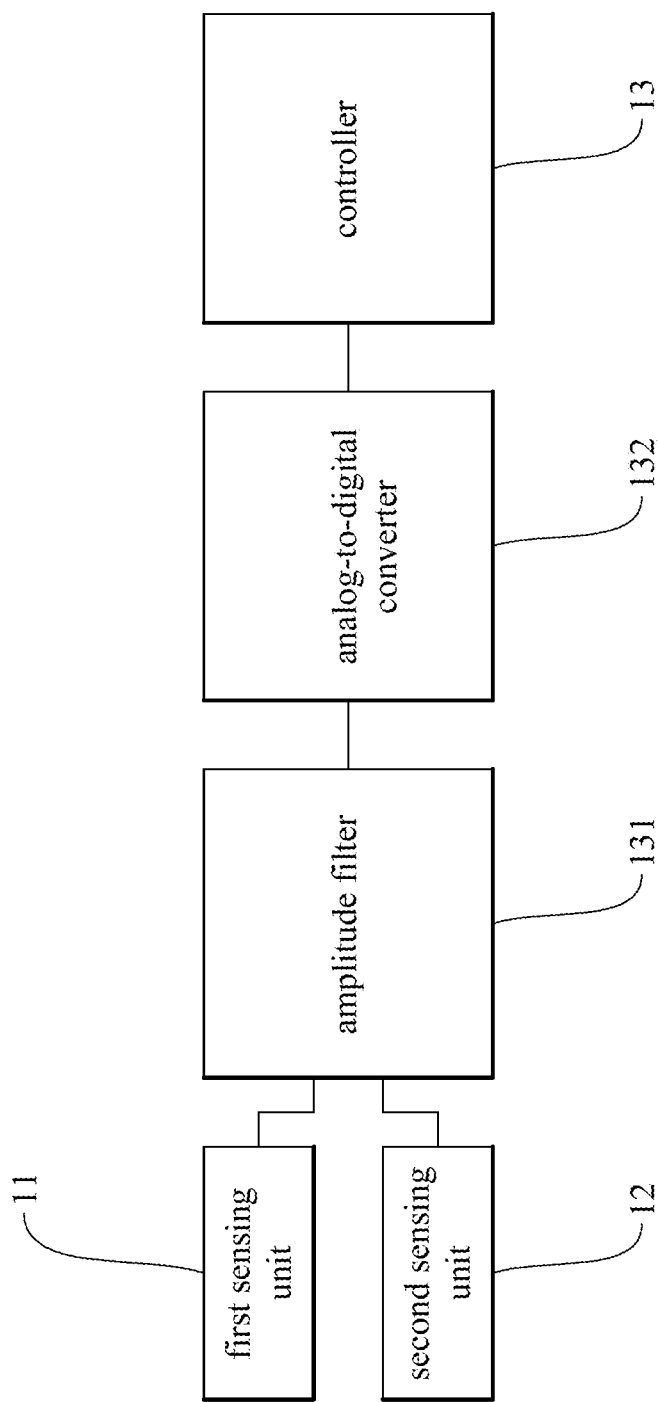
FIG. 2 is a second block diagram of a carotid blood pressure detection device according to the present invention.

The controller 13 is connected or coupled to the first sensing unit 11 and the second sensing unit 12 and is configured to work in conjunction with (or more particularly to obtain sensing data from) the first sensing unit 11 and the second sensing unit 12. The controller 13 may be a microprocessor, a digital signal processor (DSP), a programmable controller, an application-specific integrated circuit (ASIC), other similar devices, or a combination of the above. The controller 13 may be a stand-alone chip composed of a system on chip (SoC) or system in package (SiP), or an integrated circuit composed of a plurality of chips or elements that differ in function; the present invention has no limitation in this regard. As an upstream device of the sensors (i.e., the first sensing unit 11 and the second sensing unit 12), the controller 13 may be provided with an amplitude filter 131 and an analog-to-digital converter 132 as shown in FIG. 2, in order to carry out signal preprocessing, e.g., to convert the signals of the sensors into digital ones to facilitate computation.

The communication module 14 is configured to pair with the mobile device 200 or the wearable device 300, access the data obtained by the controller 13, and by means of the configuration of the mobile device 200 or the wearable device 300, output the computation result of the controller 13 to the mobile device 200 or the wearable device 300. The communication module 14 may perform wired or wireless transmission-based communication. Applicable wireless transmission methods include, for example but not limited to, Bluetooth, wireless local area network (WLAN), radio frequency identification (RFID), near-field communication (NFC), and Zigbee; the present invention has no limitation in this regard.

Figure 3:
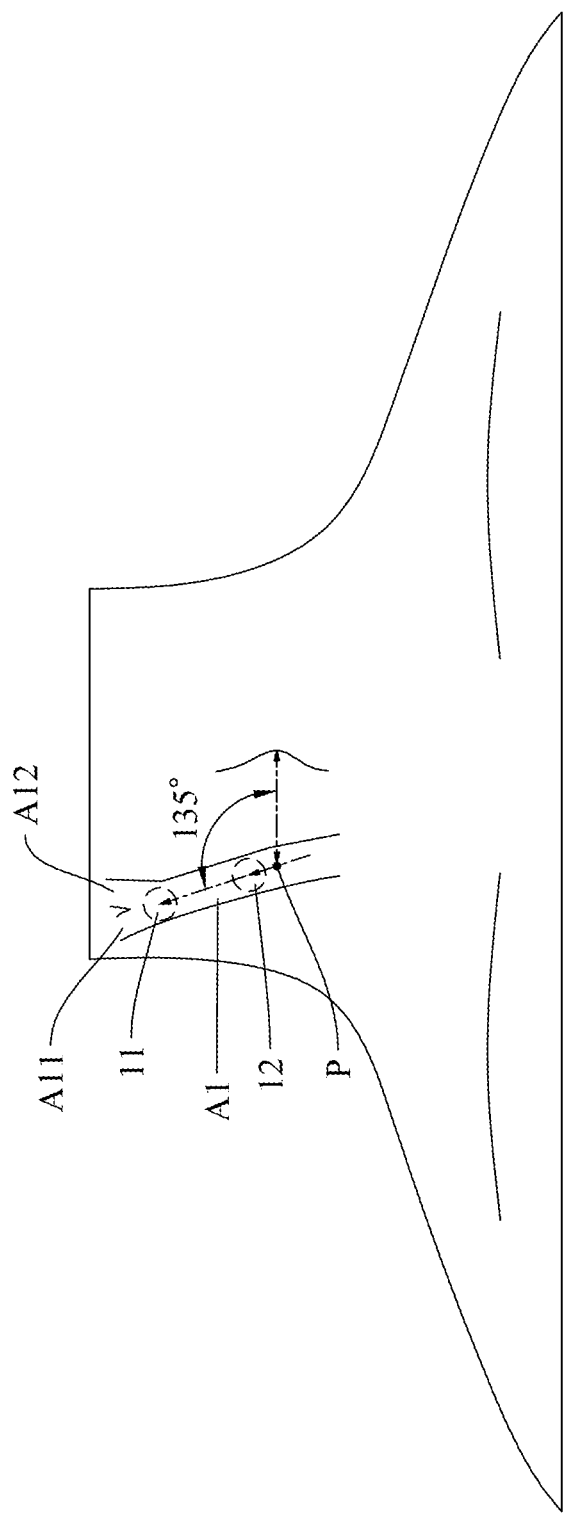
FIG. 3 is a schematic drawing that shows a state of use of a carotid blood pressure detection device according to the present invention.

Please refer to FIG. 3 for a schematic drawing that shows a state of use of a carotid blood pressure detection device according to the present invention.

As shown in FIG. 3, the carotid arteries, which are responsible for supplying blood to the brain and the neck, can be divided into two generally symmetric parts, namely a left part and a right part, each part including a common carotid artery A1 arising from the aorta and two branches (i.e., an external carotid artery A11 and an internal carotid artery A12) from the common carotid artery A1.

The external carotid artery A11 is the major source of facial blood flow and supplies blood to: the facial artery, which is in charge of the blood supply to most of the face; the internal maxillary artery, which guides blood to deeper portions of the face; and the transverse facial artery.

The other branch of the common carotid artery A1, i.e., the internal carotid artery A12, serves mainly to supply blood to brain tissues. The facial blood flow, in fact, involves intercommunication (also referred to as anatomical anastomosis) between the external and the internal carotid arteries A11 and A12; that is to say, a portion of the facial blood flow may pass through the internal carotid artery A12 via the aforesaid intercommunication. For example, the external carotid artery A11 may communicate with the internal carotid artery A12 through the internal maxillary artery or with the ophthalmic artery through the facial artery.

The facial blood flow comes mainly from the external carotid artery A11, but the external carotid artery A11 is also closely related to the internal carotid artery A12, which supplies blood directly to brain tissues and therefore may contribute to the occurrence of strokes, in three ways. First, most of the atheromatous plaque in the carotid arteries is distributed over the junction between the external and the internal carotid arteries A11 and A12; therefore, stenosis of the external carotid artery A11 tends to have a sustained effect on the atheromatous plaque in the adjacent internal carotid artery A12 or even affect the blood flow in the common carotid artery A1. Second, given the anatomical anastomosis between the internal carotid artery A12 and the external carotid artery A11, stenosis of the internal carotid artery A12 may result in the so-called steal phenomenon and hence reduce the blood flow in the same side of the face. Third, as the external carotid artery A11 accounts for 12% of the cerebral blood flow, a reduced blood flow in the neck caused by stenosis of the external carotid artery A11 is associated also with insufficient cerebral blood flow on the same side, and it is anticipated that a reduced flood flow caused by stenosis of the external carotid artery A11 may have something to do with stenosis of the internal carotid artery A12 on the same side, too. Based on the foregoing, the narrowing condition of the carotid arteries can be known if the blood flow pulses and blood flow sound in the neck are available.

To detect the flow velocity and blood flow sound in the carotid arteries, the first sensing unit 11 and the second sensing unit 12 are designed to be disposed on a subject's neck and adjacent to a first position and a second position of the subject's carotid arteries respectively. In one preferred embodiment, the first position may be the outlet of the common carotid artery A1 (i.e., the junction between the external carotid artery A11 and the internal carotid artery A12, also known as the carotid bifurcation) or any other position of the common carotid artery A1, and the second position may be any position of the common carotid artery A1 other than the first position, depending on the potential position of the disease-affected area. As the external carotid artery A11 and the internal carotid artery A12 are the two branches of the common carotid artery A1, the flow velocity in the common carotid artery A1 can be directly used to assess the possibility of atherosclerosis of the external carotid artery A11 and the internal carotid artery A12. If it is desired to assess the condition of the external carotid artery A11 or the internal carotid artery A12 alone, the positions of the first and the second sensing units 11 and 12 can be adjusted as needed. In addition to the two sensors (i.e., the first sensing unit 11 and the second sensing unit 12), the present invention may include a third sensor or even more sensors in order to sense the flow velocities and blood flow sound in different sections of the carotid arteries respectively, thereby obtaining a relatively complete set of assessment data of the common and branch carotid arteries.

Figure 4:
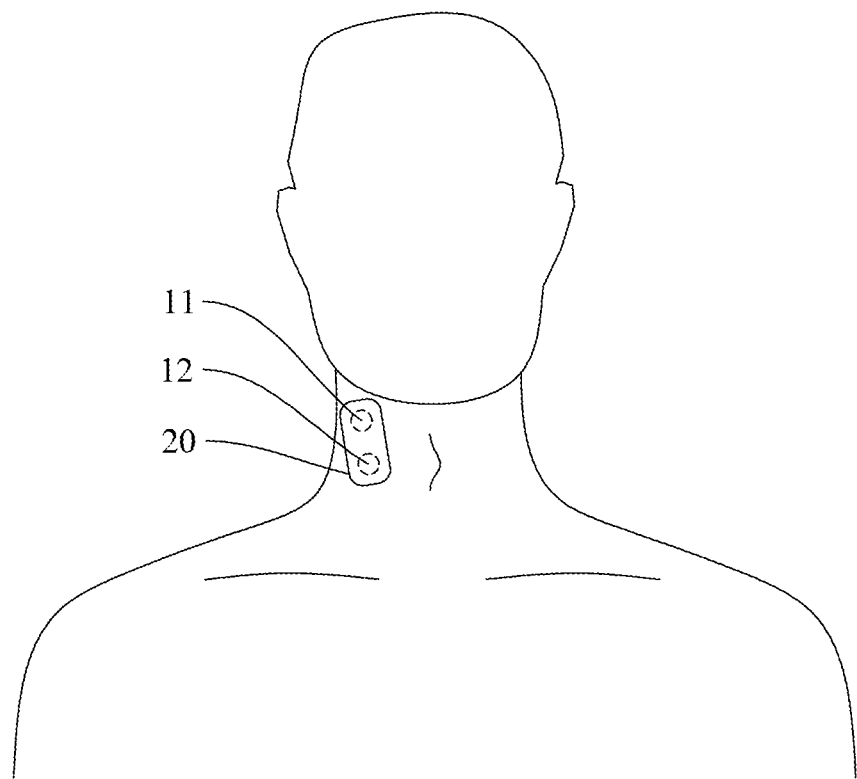
FIG. 4 is a schematic drawing that shows a state of use of the first embodiment of the present invention.

Reference is now made to FIG. 4 for a schematic drawing that shows a state of use of the first embodiment of the present invention. As shown in FIG. 4, the carotid blood pressure detection device according to this embodiment includes an adhesive patch 20, and the adhesive patch 20 is provided with the first sensing unit 11 and the second sensing unit 12. The first sensing unit 11 and the second sensing unit 12 are provided on the adhesive patch 20 in a symmetric fashion and are properly spaced apart so as correspond respectively to the first position and the second position of a subject's carotid arteries when adhesively attached to the subject's neck. In one preferred embodiment, the first sensing unit 11 and the second sensing unit 12 are fixedly connected to the adhesive patch 20 and are therefore spaced apart by a fixed distance. In another preferred embodiment, the adhesive patch 20 is provided with an adjustment enabling structure (e.g., a groove or rail) so that the distance between the first sensing unit 11 and the second sensing unit 12 can be adjusted according to practical needs. The present invention has no limitation on the adjustability of the distance between the first sensing unit 11 and the second sensing unit 12. According to yet another preferred embodiment, referring back to FIG. 3, the adhesive patch 20 is adhesively attached to a subject in the following manner. To begin with, the second sensing unit 12 on the adhesive patch 20 is aligned with and disposed at a starting point position P defined as a position 2.7 cm to 3.3 cm to the left or right of the peak of the thyroid cartilage (i.e., the laryngeal prominence). Then, the adhesive patch is held in a slanting manner such that the line connecting the first sensing unit 11 to the second sensing unit 12 forms an included angle of 135 degrees with the line connecting the starting point position P and the laryngeal prominence, wherein the included angle is measured upward from the line connecting the starting point position P and the laryngeal prominence. It should be pointed out that FIG. 3 shows the subject in front view, that the surface of the neck is curved, and that therefore the included angle of 135 degrees cannot be accurately shown. FIG. 3 as well as the other accompanying drawings is not intended to be restrictive of the scope of the invention after all.

Figure 5:
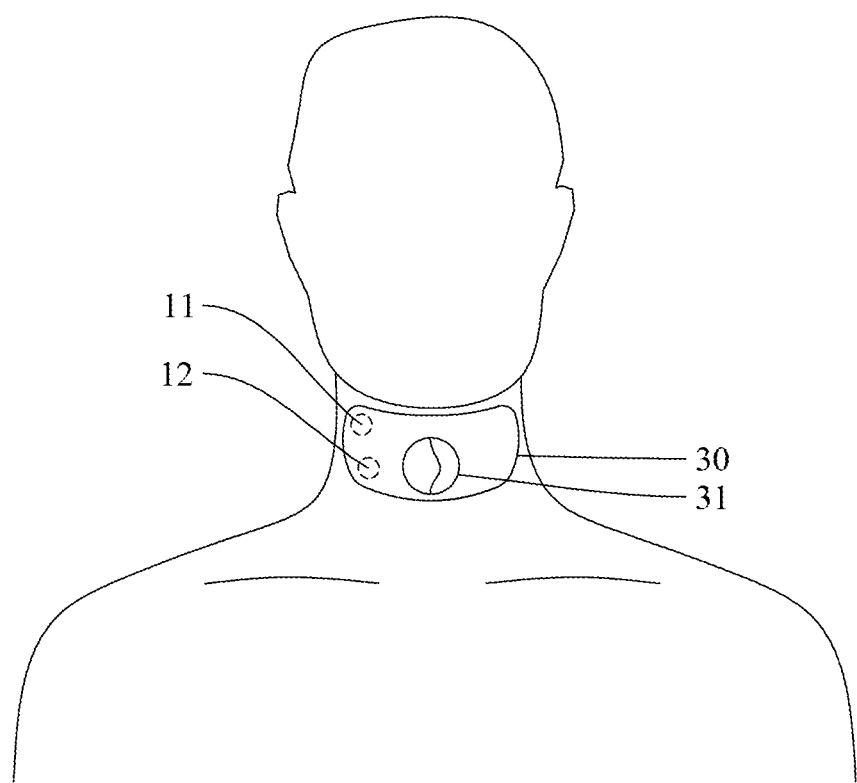
FIG. 5 is a schematic drawing that shows a state of use of the second embodiment of the present invention.

FIG. 5 schematically shows a state of use of the second embodiment of the present invention. As shown in FIG. 5, the carotid blood pressure detection device according to this embodiment includes an adhesive patch 30, on which the first sensing unit 11 and the second sensing unit 12 are provided. The adhesive patch 30 is further provided with a thyroid cartilage locating hole 31. The first sensing unit 11 and the second sensing unit 12 are provided on one side of the thyroid cartilage locating hole 31 and are properly spaced apart so as to correspond respectively to the first position and the second position of a subject's carotid arteries when adhesively attached to the subject's neck. In one preferred embodiment, the first sensing unit 11 and the second sensing unit 12 are fixedly connected to the adhesive patch 30 and are therefore spaced apart by a fixed distance. In another preferred embodiment, the adhesive patch 30 is provided with an adjustment enabling structure (e.g., a groove or rail) so that the distance between the first sensing unit 11 and the second sensing unit 12 can be adjusted according to practical needs. As previously mentioned, the invention has no limitation on the adjustability of the distance between the first sensing unit 11 and the second sensing unit 12.

In order to obtain the optimal detection data, referring back to FIG. 3, the positions at which the first sensing unit 11 and the second sensing unit 12 are respectively provided on the adhesive patch 30 in this preferred embodiment are determined as follows. To start with, a starting point position P is defined as a position 2.7 cm to 3.3 cm to the left or right of the thyroid cartilage locating hole 31, and a specific direction is defined as the direction that forms an included angle of 135 degrees with the line connecting the starting point position P and the thyroid cartilage locating hole 31, wherein the included angle is measured upward from the line connecting the starting point position P and the thyroid cartilage locating hole 31. The first sensing unit 11 is provided at a position that is 0 cm to 4 cm away from the starting point position P in the aforesaid direction, and the second sensing unit 12 is provided at a position that is 0 cm to 4 cm away from the starting point position P in the same direction and that does not coincide with the first sensing unit 11. It should be reiterated that FIG. 3 shows the subject in front view, that the surface of the neck is curved, and that therefore the included angle of 135 degrees cannot be accurately shown. None of the accompanying drawings is intended to be restrictive of the scope of the invention.

Figure 6:
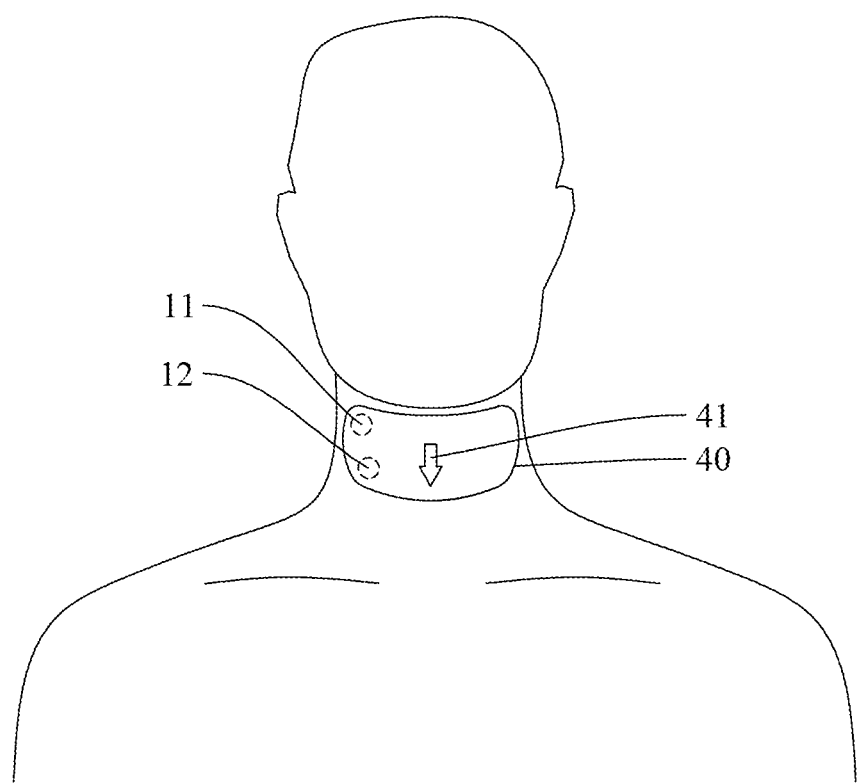
FIG. 6 is a schematic drawing that shows a state of use of the third embodiment of the present invention.

FIG. 6 schematically shows a state of use of the third embodiment of the present invention. As shown in FIG. 6, the carotid blood pressure detection device according to this embodiment includes an adhesive patch 40, on which the first sensing unit 11 and the second sensing unit 12 are provided. The adhesive patch 40 is further provided with a thyroid cartilage locating mark 41. The first sensing unit 11 and the second sensing unit 12 are provided on one side of the thyroid cartilage locating mark 41 and are properly spaced apart so as to correspond respectively to the first position and the second position of a subject's carotid arteries when adhesively attached to the subject's neck. In one preferred embodiment, the first sensing unit 11 and the second sensing unit 12 are fixedly connected to the adhesive patch 40 and are therefore spaced apart by a fixed distance. In another preferred embodiment, the adhesive patch 40 is provided with an adjustment enabling structure (e.g., a groove or rail) so that the distance between the first sensing unit 11 and the second sensing unit 12 can be adjusted according to practical needs. As stated above, the invention has no limitation on the adjustability of the distance between the first sensing unit 11 and the second sensing unit 12.

In order to obtain the optimal detection data, referring again to FIG. 3, the positions at which the first sensing unit 11 and the second sensing unit 12 are respectively provided on the adhesive patch 40 in this preferred embodiment are determined as follows. To start with, a starting point position P is defined as a position 2.7 cm to 3.3 cm to the left or right of the thyroid cartilage locating mark 41, and a specific direction is defined as the direction that forms an included angle of 135 degrees with the line connecting the starting point position P and the thyroid cartilage locating mark 41, wherein the included angle is measured upward from the line connecting the starting point position P and the thyroid cartilage locating mark 41. The first sensing unit 11 is provided at a position that is 0 cm to 4 cm away from the starting point position P in the aforesaid direction, and the second sensing unit 12 is provided at a position that is 0 cm to 4 cm away from the starting point position P in the same direction and that does not coincide with the first sensing unit 11. It should be reiterated that FIG. 3 shows the subject in front view, that the surface of the neck is curved, and that therefore the included angle of 135 degrees cannot be accurately shown. None of the accompanying drawings is intended to be restrictive of the scope of the invention.

The calculations involved in the present invention are detailed as follows.

The heart pumps blood into the aorta in a pulsing manner. The wall of the aorta, therefore, generates pulse pressure waves, which propagate to the downstream blood vessels at a certain velocity along the blood vessel walls. The velocity at which such pulse pressure waves propagate along the artery walls is referred to as the pulse wave velocity (PWV).

The PWV is related to such factors as the biophysical properties of the artery walls, the geometric properties of the blood vessels involved, and the density of blood. The value of the PWV is an early sensitive indicator of the stiffness (or narrowness) of the arteries. The larger the value, the stiffer the blood vessel walls (or the narrower the blood vessels). The standard/normal PWV is 140 mm/ms.

The PWV of a carotid artery can be calculated from the pulse wave propagation time and distance between two artery recording positions (e.g., the position where a common carotid artery originates from the aorta and a predetermined position of the common carotid artery), the equation for the calculation being:

$$PWV = \frac{L}{t} \text{ (mm/ms)},$$

where t is the time difference between two adjacent waveforms, i.e., the propagation time, and L is the distance between the two artery sensors, i.e., the propagation distance.

An increase in the PWV of a carotid artery implies an increase in the stiffness (or narrowness) of the carotid artery and a decrease in the compliance of the carotid artery. Conversely, a carotid artery with a low PWV has low stiffness and high compliance. Age and blood pressure are the main factors that influence the PWV, and antihypertensive therapy currently remains the most effective method for reducing the PWV.

Calculation of the carotid PWV is based on the relationship between pressure and the PWV. In each cardiac cycle, the contraction of the left ventricle generates a pressure pulse that propagates through the arteries to the very ends of those blood vessels. The PWV of an artery is a function of the stiffness of the artery, as can be expressed by equation (a):

$$PWV = \sqrt{\left(\frac{V}{\rho}\right)\left(\frac{dP}{dV}\right)}, \quad \text{equation (a)}$$

where $\rho$ is the density of blood.

The stiffness of a carotid artery is associated with the transmural pressure across the artery wall, and this pressure is a function of the geometry of the blood vessel and the viscoelasticity of the blood vessel wall. As the pressure acting on an artery wall from outside the artery is typically negligible, the stiffness and PWV of a carotid artery are a function of the artery, and the pulses in propagation form the basis of carotid stenosis measurement.

More specifically, correlation between the PWV and arterial pressure forms the basis of non-invasive blood pressure measurement. In particular, the PWV has the strongest correlation to diastolic pressure and mean arterial pressure, as can be expressed by equation (b):

$$PWV = fcn(MAP) \quad \text{equation (b)}.$$

The relationship between the PWV and mean arterial pressure can be accurately described by the following linear model equation (c):

$$PWV(t) = a \cdot MAP(t) + pwv_0 \quad \text{equation (c)},$$

where the slope a and the constant $pwv_0$ are subject-specific parameters.

To trace a patient's pulse pressure and velocity, the present invention uses the first sensing unit 11 and the second sensing unit 12 to monitor a known parameter, i.e., the pulse arrival time (PAT). Each pulse arrival time measurement is in fact the sum of two different periods of time, namely the vascular transit time (VTT) and the pre-ejection period (PEP). The vascular transit time is the time for which a pressure pulse travels along an arterial path. The pre-ejection period is the time interval between two adjacent peaks of a composite wave, or the interval at which the aortic valve opens, and includes electromechanical delay and isovolumic contraction. The pulse arrival time can be expressed by equation (d):

$$PAT = VTT + PEP = \left(\frac{L_t}{PWV}\right) + PEP, \quad \text{equation (d)}$$

where the parameter $L_t$ is the length of the path along which a pressure pulse propagates in an artery.

Assuming the pre-ejection period is constant while monitoring takes place, a change in the vascular transit time directly results in a change in the pulse arrival time, and these two parameters are associated with variation of the mean arterial pressure. To establish the relationship between pulse arrival time and mean arterial pressure and the linear relationship between mean arterial pressure and PWV, it behaves as if equation (b) must be abstracted and defined in measuring the pulse delay time at the individual measurement pulse arrival time, as expressed by equation (e):

$$PAT = \left(\frac{L_t}{PWV}\right) = \left(\frac{L_t}{aMAP + pwv_0}\right). \quad \text{equation (e)}$$

In one preferred embodiment, mean arterial pressure is obtained through the following equation (I):

$$\text{mean arterial pressure } (MAP) = a\left(\frac{l_p}{t_{pa}} \times c\right) + b, \quad \text{equation (I)}$$

where $l_p$ is the length of the path between the first position and the second position; $t_{pa}$ is the times it takes for a pulse to reach the second position from the first position; and a, b, and c are correction parameters. The correction parameters are derived from a target subject database to provide necessary adjustment to the calculation.

In another preferred embodiment, mean arterial pressure is obtained through the following equation (II):

$$\text{mean arterial pressure } (MAP) = A\left(\frac{l_p}{t_{pa}} \times C\right)^2 + B, \quad \text{equation (II)}$$

where $l_p$ is the length of the path between the first position and the second position; $t_{pa}$ is the times it takes for a pulse to reach the second position from the first position; and A, B, and C are correction parameters. The correction parameters are derived from a target subject database to provide necessary adjustment to the calculation.

In either of equations (I) and (II), mean arterial pressure is derived from the time difference between the pulse response at the first position and that at the second position. In one preferred embodiment, the time it takes for a pulse to reach the second position from the first position is obtained by measuring the time difference between a peak value detected by the first sensing unit 11 and the corresponding peak value detected by the second sensing unit 12. In another preferred embodiment, the time it takes for a pulse to reach the second position from the first position is obtained by measuring the time difference between a signal valley detected by the first sensing unit 11 and the corresponding signal valley detected by the second sensing unit 12, wherein the measurement is triggered by the signal valleys. The present invention has no limitation on the method by which to determine the time it takes for a pulse to reach the second position from the first position.

Through the foregoing calculations, the blood flow velocity in a target section of the subject's carotid arteries (i.e., the section between the first position and the second position of the carotid arteries) can be obtained, and mean arterial pressure (MAP) can be derived from the blood flow velocity obtained. The severity of atherosclerosis of the target arterial section can then be assessed by analyzing the mean arterial pressure. The aforesaid data can also be provided to caregivers as a way to achieve real-time monitoring.

Apart from the controller 13 of the carotid blood pressure detection device 100, the afore-mentioned calculations may be performed by a program installed in the mobile device 200 or the wearable device 300 and be controlled by a controller in the mobile device 200 or the wearable device 300 instead, in order to reduce the power required by the carotid blood pressure detection device 100, allow the controller 13 of the carotid blood pressure detection device 100 to be miniaturized, and decrease the weight of the carotid blood pressure detection device 100.

Figure 7:
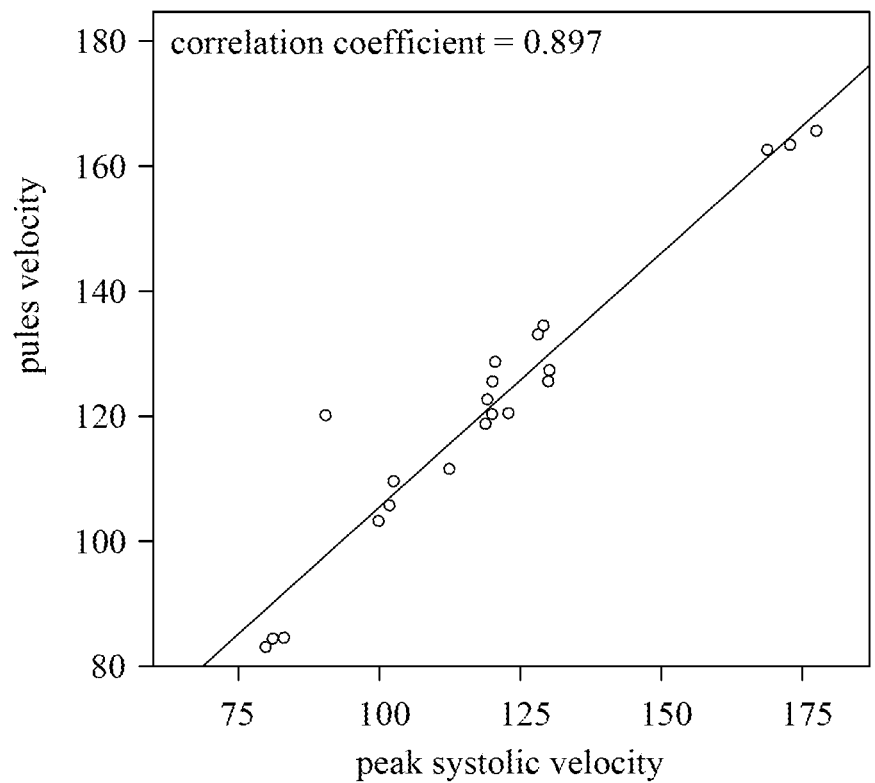
FIG. 7 is a first plot showing the test result of the correlation between the present invention and a commercially available product.

FIG. 7 is a plot showing the test result of the correlation between the present invention and a commercially available product.

To determine whether the arterial PWV measured by the present invention differs from the measurement result of a commercially available product, the inventor of the invention conducted a carotid pressure measurement study in which the carotid PWVs of a group of subjects (including healthy people and those with heart rhythm irregularities) were recorded using a commercially available vascular screening device (Fukuda Denshi VS-1500) as well as the carotid blood pressure detection device 100 of the invention, and in which a correlation analysis was performed on the measurement results of the two devices.

As shown in FIG. 7, during the 30 seconds when carotid pressure measurements were taken simultaneously with the carotid blood pressure detection device 100 of the present invention and Fukuda Denshi VS-1500, there was a significant correlation, or a linear relationship, between the PWVs recorded by the carotid blood pressure detection device 100 and those recorded by Fukuda Denshi VS-1500, the correlation coefficient R being 0.897.

Figure 8:
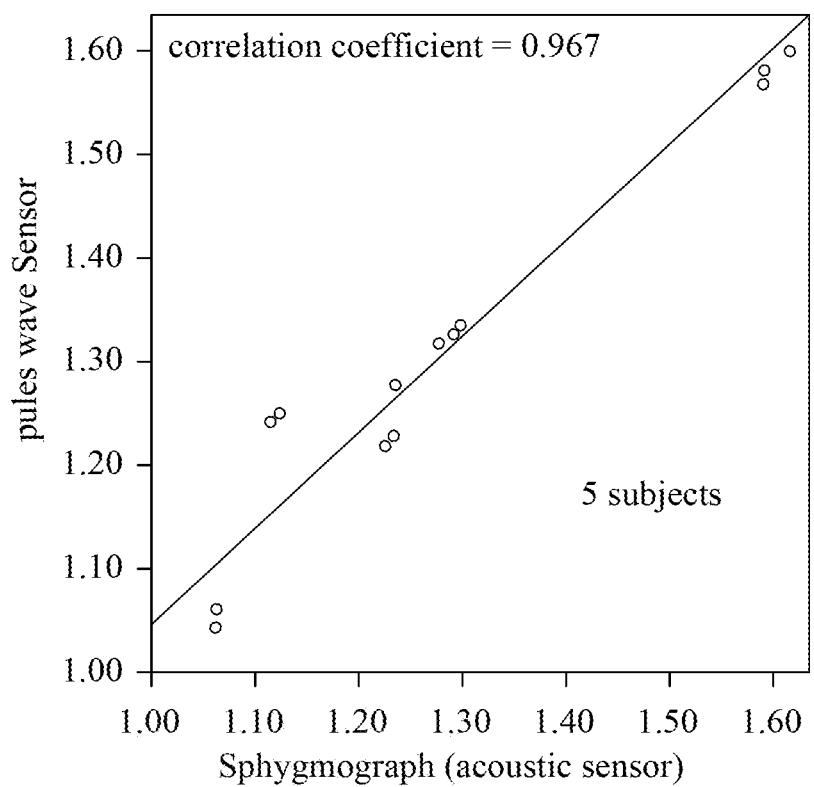
FIG. 8 is a second plot showing the test result of the correlation between the present invention and a commercially available product.
Figure 9:
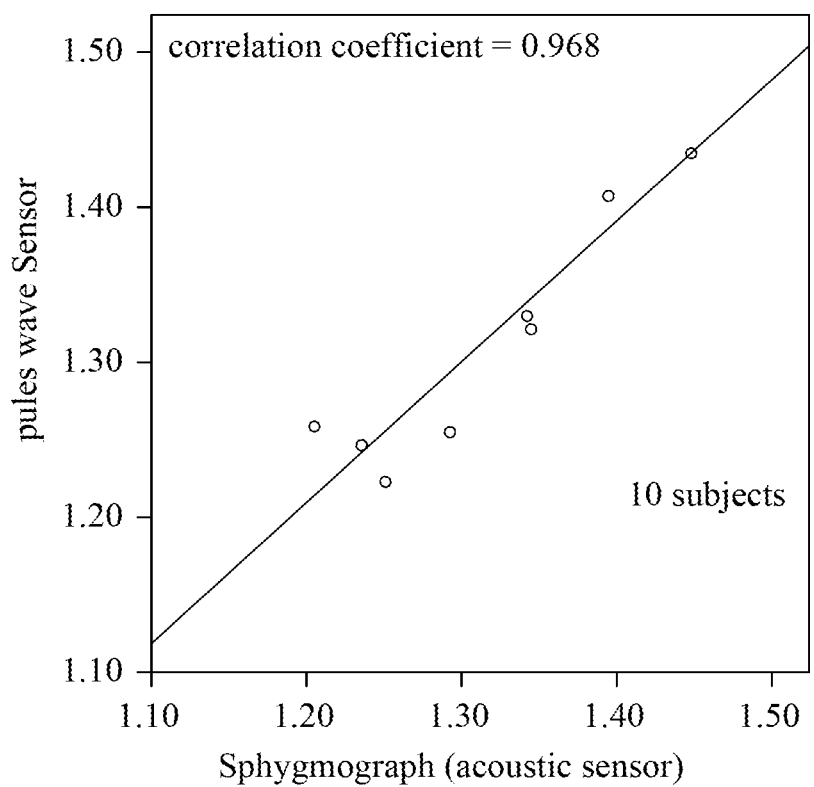
FIG. 9 is a third plot showing the test result of the correlation between the present invention and a commercially available product.
Figure 10:
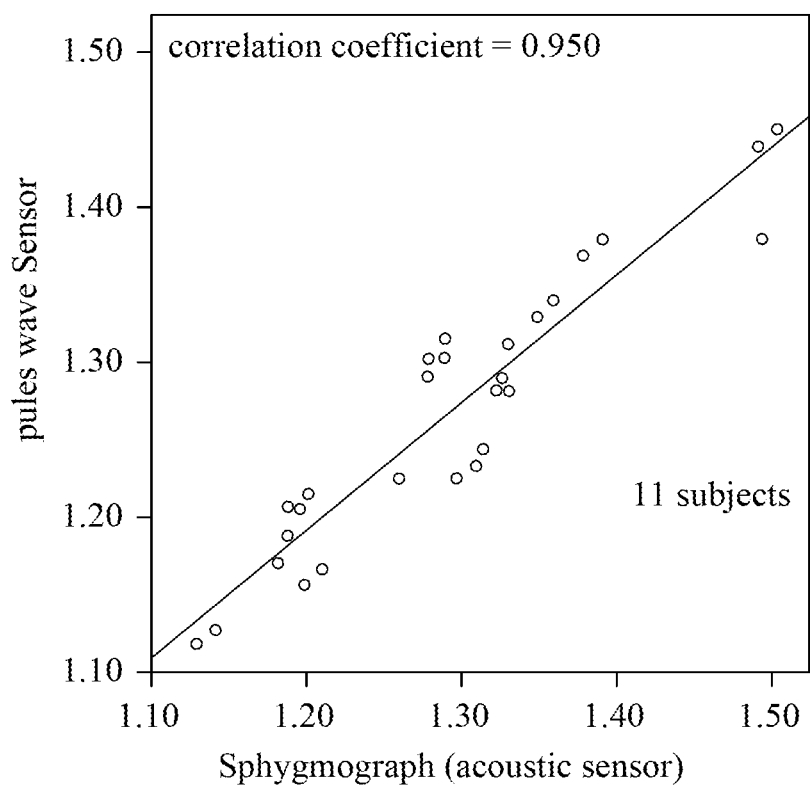
FIG. 10 is a fourth plot showing the test result of the correlation between the present invention and a commercially available product.

FIG. 8, FIG. 9, and FIG. 10 are plots showing more test results of the correlation between the present invention and the commercially available product, as detailed below.

In another multiple-subject carotid pressure measurement study, the carotid PWVs of three subject groups of different sizes were recorded using Fukuda Denshi VS-1500 as well as the carotid blood pressure detection device 100 of the present invention, and a correlation analysis was performed on the measurement results of the two devices.

As shown in FIG. 8, which presents the correlation analysis result for the group consisting of five subjects, there was a significant correlation, or a linear relationship, between the PWVs recorded by the carotid blood pressure detection device 100 of the present invention and those recorded by Fukuda Denshi VS-1500 during the 30 seconds when carotid pressure measurements were taken simultaneously with the carotid blood pressure detection device 100 and Fukuda Denshi VS-1500, the correlation coefficient R being 0.967.

As shown in FIG. 9, which presents the correlation analysis result for the group consisting of ten subjects, there was a significant correlation, or a linear relationship, between the PWVs recorded by the carotid blood pressure detection device 100 of the present invention and those recorded by Fukuda Denshi VS-1500 during the 30 seconds when carotid pressure measurements were taken simultaneously with the carotid blood pressure detection device 100 and Fukuda Denshi VS-1500, the correlation coefficient R being 0.968.

As shown in FIG. 10, which presents the correlation analysis result for the group consisting of eleven subjects, there was a significant correlation, or a linear relationship, between the PWVs recorded by the carotid blood pressure detection device 100 of the present invention and those recorded by Fukuda Denshi VS-1500 during the 30 seconds when carotid pressure measurements were taken simultaneously with the carotid blood pressure detection device 100 and Fukuda Denshi VS-1500, the correlation coefficient R being 0.950.

Figure 11:
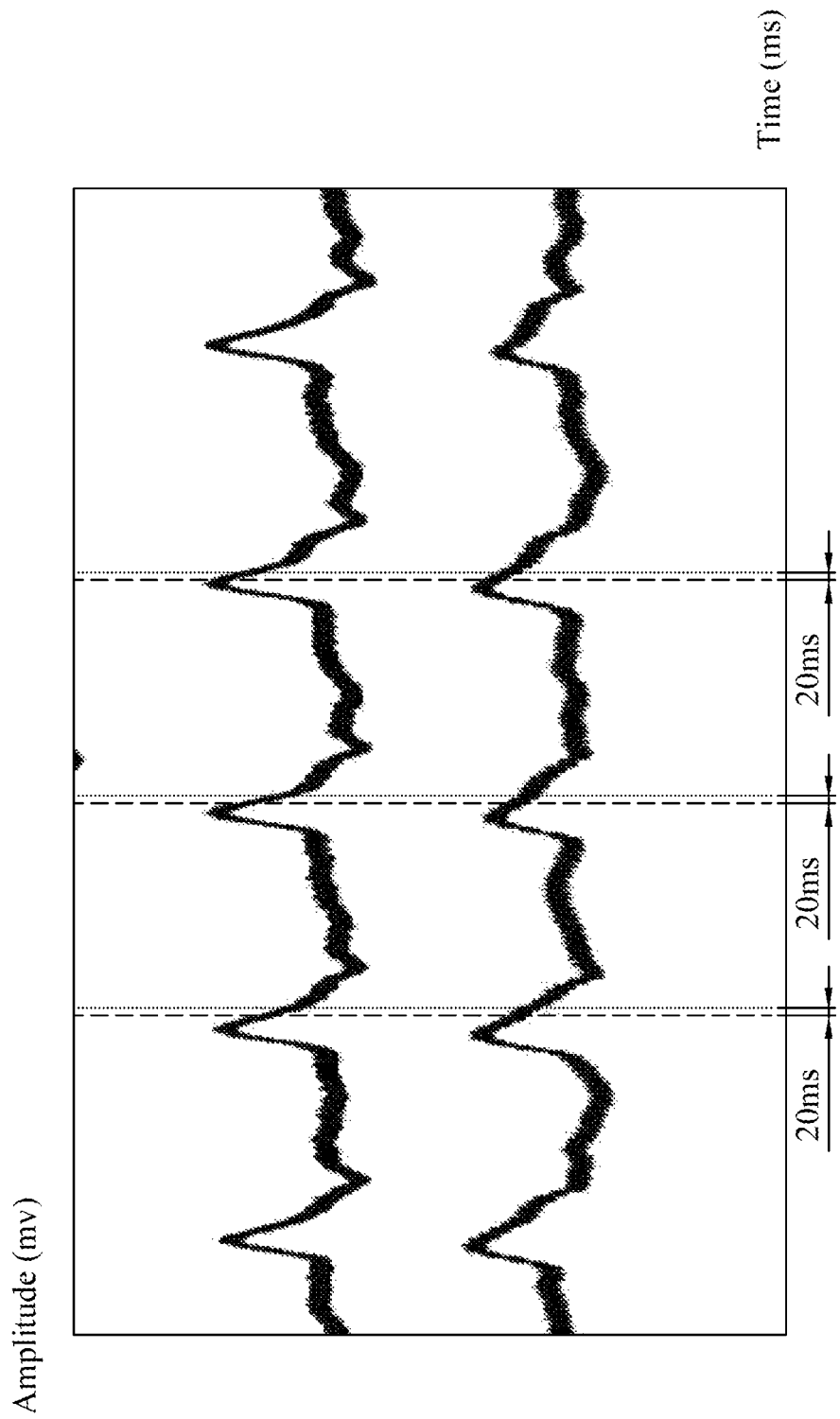
FIG. 11 shows an oscillogram corresponding to an arrangement in which the sensors of the present invention are spaced apart by 3 cm.

Please refer to FIG. 3 in conjunction with FIG. 11, which shows an oscillogram corresponding to an arrangement in which the sensors of the present invention are spaced apart by 3 cm.

The inventor of the present invention conducted yet another study in which the first sensing unit 11 and the second sensing unit 12 were disposed on a subject's neck at various intervals. The second position, to which the second sensing unit 12 corresponds, was fixed and was determined as follows. First, an imaginary line was drawn downward from the middle point of the subject's lips to find the most prominent point of the subject's neck as a center point. Then, the point on the subject's neck that was 3 cm leftward of the center point was defined as a starting point, which indicates the location of the second position, and the second sensing unit 12 was disposed at the starting point. The position of the first sensing unit 11 was varied, including a series of five positions that were sequentially spaced apart from the starting point at a 1 cm increment along the extending direction of the common carotid artery A1; in other words, the five positions of the first sensing unit 11 were spaced apart from the starting point by 1 cm, 2 cm, 3 cm, 4 cm, and 5 cm respectively. Valid peaks were obtained from each of the oscillograms corresponding respectively to the 1 cm to 4 cm spacing. The oscillogram corresponding to the 1 cm spacing showed a slight deviation, but most of the peaks were effectively obtained. A plurality of waveforms were effectively obtained from the oscillograms corresponding respectively to the 2 cm to 4 cm spacing. The waveforms in the 5 cm-spacing oscillogram were too vague to be detected. The PWVs detected were summarized in the following table:

| Spacing (cm) | 1 | | | 2 | | | 3 | | | 4 | | | 5 | | |
|---|---|---|---|---|---|---|---|---|---|---|---|---|---|---|---|
| Sampling times of 3 repetitions | 15 | 10 | 15 | 15 | 15 | 15 | 20 | 20 | 20 | 30 | 30 | 30 | X | X | X |
| Average sampling | | 13.3 | | | 15 | | | 20 | | | 30 | | | Undetectable | | |

During the sensing process, the sensing structure was adjusted to suit the curvature of the subject's neck in order for the sensors to lie compliantly on the skin. In addition, temporal calibration was performed to a certain degree on the waveforms obtained. It can be known from the table above that the first sensing unit 11 and the second sensing unit 12 are preferably spaced apart by a distance ranging from 1 cm to 4 cm. The range from 1 cm to 4 cm, however, is by no means limiting.

The inventor of the present invention has found after repeated tests that most of the peaks in a subject's oscillogram can be effectively obtained if the sensing units (i.e., the first sensing unit 11 and the second sensing unit 12) are disposed respectively at a starting point position defined as a position approximately 3 cm to the left or right of the most prominent point of the subject's neck that lies right below the middle point of the subject's lips and a position 0 cm to 4 cm away from the starting point position along a direction that forms a 135-degree included angle with the line connecting the starting point position and the most prominent point of the neck, wherein the included angle is measured upward from the line connecting the starting point position and the most prominent point. More specifically, the starting point position may be a position 2.7 cm to 3.3 cm (e.g., 2.7 cm, 2.8 cm, 2.9 cm, 3.0 cm, 3.1 cm, 3.2 cm, or 3.3 cm, without limitation) to the left or right of the most prominent point of the subject's neck that lies right below the middle point of the subject's lips.

As above, the present invention makes effective use of sensors to detect the pressure of the carotid arteries so that a senior patient can be rapidly screened for carotid stenosis. In addition, the invention can be used in a fast-screening test because it effectively reduces the examination time required by such conventional methods as DSA, MRA, and Doppler ultrasound scanning.

The above is the detailed description of the present invention. However, the above is merely the preferred embodiment of the present invention and cannot be the limitation to the implement scope of the present invention, which means the variation and modification according to the present invention may still fall into the scope of the invention.

What is claimed is:

1. A carotid blood pressure detection device, comprising: a first sensing unit is configured to be disposed on a subject's neck and adjacent to a first position of the subject's carotid arteries; a second sensing unit is configured to be disposed on the subject's neck and adjacent to a second position of the subject's carotid arteries; and a controller connected or coupled to the first sensing unit and the second sensing unit, wherein the controller derives a mean arterial pressure of a section of the subject's carotid arteries that lies between the first position and the second position of the subject's carotid arteries from pulse wave data measured and obtained by the first sensing unit and pulse wave data measured and obtained by the second sensing unit, wherein the first sensing unit is a Doppler radar, a pressure sensor, an acoustic wave sensor, an ultrasound sensor, or a photoplethysmographic sensor, the second sensing unit is a Doppler radar, a pressure sensor, an acoustic wave sensor, an ultrasound sensor, or a photoplethysmographic sensor, wherein the mean arterial pressure is obtained through one of the following equation:

$$MAP = a\left(\frac{l_p}{t_{pa}} \times c\right) + b,$$

or $$MAP = A\left(\frac{l_p}{t_{pa}} \times C\right)^2 + B,$$

and wherein MAP is the mean arterial pressure; lp is a length of a path between the first position and the second position; tpa is times it takes for a pulse to reach the second position from the first position; and a, b, and c and A, B, and C are correction parameters.

2. The carotid blood pressure detection device of claim 1, wherein the first sensing unit and the second sensing unit are spaced apart by a distance ranging from 1 cm to 4 cm.

3. The carotid blood pressure detection device of claim 1, wherein the carotid blood pressure detection device further includes an adhesive patch, and the adhesive patch is provided with the first sensing unit and the second sensing unit.

4. The carotid blood pressure detection device of claim 3, wherein the adhesive patch is provided with a thyroid cartilage locating hole or a thyroid cartilage locating mark, and the first sensing unit and the second sensing unit are provided on one side of the thyroid cartilage locating hole or the thyroid cartilage locating mark and are properly spaced apart.

5. The carotid blood pressure detection device of claim 4, wherein the positions at which the first sensing unit and the second sensing unit are respectively provided on the adhesive patch are determined as follows: a starting point position is defined as a position 2.7 cm to 3.3 cm to the left or right of the thyroid cartilage locating hole or the thyroid cartilage locating mark, and a specific direction is defined as a direction that forms an included angle of 135 degrees with a line connecting the starting point position and the thyroid cartilage locating hole or the thyroid cartilage locating mark, wherein the included angle is measured upward from the line connecting the starting point position and the thyroid cartilage locating hole or the thyroid cartilage locating mark; wherein, the first sensing unit is provided at a position that is 0 cm to 4 cm away from the starting point position in aforesaid direction, and the second sensing unit is provided at a position that is 0 cm to 4 cm away from the starting point position in same direction and that does not coincide with the first sensing unit.

6. The carotid blood pressure detection device of claim 4, wherein the positions at which the first sensing unit and the second sensing unit are respectively provided on are determined as follows: a starting point position is defined as a position 2.7 cm to 3.3 cm leftward of a center point defined as a peak of the thyroid cartilage of the subject's neck that lies right below the middle point of the subject's lips, and a specific direction is defined as a direction that forms an included angle of 135 degrees with a line connecting the starting point position and the thyroid cartilage locating hole or the thyroid cartilage locating mark, wherein the included angle is measured upward from the line connecting the starting point position and the center point; wherein, the first sensing unit is provided at a position that is 0 cm to 4 cm away from the starting point position in aforesaid direction, and the second sensing unit is provided at a position that is 0 cm to 4 cm away from the starting point position in same direction and that does not coincide with the first sensing unit.

7. The carotid blood pressure detection device of claim 1, wherein the carotid blood pressure detection device further includes a communication module connected to the controller.

8. The carotid blood pressure detection device of claim 7, wherein the communication module performs wireless transmission-based communication, and the applicable wireless transmission methods include Bluetooth, wireless local area network (WLAN), radio frequency identification (RFID), near-field communication (NFC), and Zigbee.

9. The carotid blood pressure detection device of claim 7, wherein the controller is connected or coupled to a mobile device or a wearable device via the communication module to access the data of the controller through the mobile device or the wearable device.

* * * * *